United States Patent
Intintoli et al.

(10) Patent No.: US 6,893,432 B2
(45) Date of Patent: May 17, 2005

(54) LIGHT-DISPERSIVE PROBE

(75) Inventors: Alfred J. Intintoli, West Chester, PA (US); Dwight Franz, Haddonfield, NJ (US)

(73) Assignee: Surgical Laser Technologies, Inc., Montgomeryville, PA (US)

(*) Notice: Subject to any disclaimer, the term of this patent is extended or adjusted under 35 U.S.C. 154(b) by 0 days.

(21) Appl. No.: 10/104,511

(22) Filed: Mar. 22, 2002

(65) Prior Publication Data

US 2002/0138073 A1 Sep. 26, 2002

Related U.S. Application Data

(60) Provisional application No. 60/278,177, filed on Mar. 23, 2001.

(51) Int. Cl.[7] .............................................. A61B 18/22
(52) U.S. Cl. ........................................... 606/2; 606/15
(58) Field of Search ....................................... 606/2–18

(56) References Cited

U.S. PATENT DOCUMENTS

| | | | |
|---|---|---|---|
| 4,592,353 A | 6/1986 | Daikuzono | 128/303.1 |
| 4,660,925 A | 4/1987 | McCaughan | 350/96.15 |
| 4,693,556 A | 9/1987 | McCaughan | 350/320 |
| 5,054,867 A | 10/1991 | Wagnieres et al. | 385/31 |
| 5,219,346 A * | 6/1993 | Wagnieres et al. | 606/16 |
| 5,269,777 A | 12/1993 | Doiron et al. | 606/7 |
| 5,380,318 A | 1/1995 | Daikuzono | 606/16 |
| 5,431,647 A | 7/1995 | Purcell et al. | 606/16 |
| 5,520,681 A | 5/1996 | Fuller et al. | 606/17 |
| 5,536,265 A | 7/1996 | Van den Bergh et al. | 606/2 |
| 5,632,767 A | 5/1997 | Sinofsky | 607/89 |
| 5,807,390 A | 9/1998 | Fuller et al. | 606/17 |
| 5,908,415 A | 6/1999 | Sinofsky | 606/7 |
| 5,947,959 A * | 9/1999 | Sinofsky | 606/15 |

* cited by examiner

Primary Examiner—Linda C. M. Dvorak
Assistant Examiner—Aaron Roane
(74) Attorney, Agent, or Firm—Drinker Biddle & Reath LLP

(57) ABSTRACT

A surgical probe is disclosed that disperses light sideways from its fore end. A light-dispersive and light-transmissive medium is enclosed within a housing. The medium is preferably divided into sections containing different concentrations of a light-dispersing material within a matrix. The sections are preferably separated by non-dispersive spacers. At the tip end of the probe is preferably a mirror to reflect the light back into the dispersive medium. The mirror may consist of layers with multiple indexes of refraction. By these features, especially in combination, the directionality and intensity distribution of the emitted light may be controlled. The present invention is designed to be useful especially in the use of laser energy in the percutaneous, interstitial irradiation of tissue growths.

39 Claims, 3 Drawing Sheets

LIGHT-DISPERSIVE PROBE

CROSS-REFERENCE TO RELATED APPLICATION

The benefit of the filing date of U.S. provisional patent application Ser. No. 60/278,177, filed Mar. 23, 2001, is hereby claimed. The entire disclosure of the aforesaid provisional application is incorporated herein by reference.

FIELD OF THE INVENTION

The present invention relates to a surgical probe that operates in conjunction with a source of light and a conduit by which the light is conveyed from the source of light to the probe. The invention relates particularly to a light-emitting probe that disperses light over a substantial length of the tip of the probe.

BACKGROUND OF THE INVENTION

Surgeons have for many years used laser energy as a preferred means of light energy to achieve a variety of surgical effects. Among other effects, such energy can cut, vaporize, ablate or coagulate tissue. Based on various parameters, it is possible to irradiate diseased tissue, and cause its coagulation and necrosis, without injuring in a significant degree adjacent tissue that is healthy. It is known in hyperthermia, for example, that carcinogenic tissue, being weaker than healthy tissue, will necrose when exposed to temperatures from ca. 42 to 45 degrees Celsius, whereas healthy tissue, in general, will begin to necrose when heated to ca. 60 degrees Celsius.

When used interstitially, a probe is inserted into the tissue to be treated. In some interstitial cases, the surgeon desires to irradiate a generally spheroidal pattern about the fore end of the probe, and desires that the irradiation should be of dispersed, uniform intensity and thus progressively yield a controlled zone of necrotic destruction. The emission of light at the fore end of the probe is therefore both radial, or sideward, and axial, or forward. In other cases, as for example in order to achieve a cylindrical or ellipsoidal pattern of tissue destruction about the probe, only radial or sideward emission is desirable, and axial or forward emission is not. Typically, it is preferred that the radial emission should be dispersed over a predetermined surface area of the probe and at a generally uniform intensity. More and more, such probes are used percutaneously, and it is then desirable to use a tracking means to determine their location. It is then desirable to make the probe conspicuously visible using such a tracking device.

When operating intraluminally, as for example in atherosclerotic vessels, a surgeon may desire irradiation patterns similar to those in interstitial use. In some cases, the surgeon may even use a probe that can, to a limited degree, irradiate tissue that lies aft of the probe.

Generally, laser light that is conducted from a source of laser energy through a fiber-optic cable will not be emitted when it encounters the boundary of the light-conductive core of the fiber-optic material. The boundary is a smooth interface between the core of the fiber and a cladding about the core. The indexes of refraction of the cladding and core are selected such that the light is kept inside the core by total internal reflection until it is conducted to the distal end of the fiber-optic. Moreover, the light that may be emitted from the distal end of the fiber-optic cable will typically manifest a Gaussian intensity distribution: a preponderance of the emitted light is directed parallel, or nearly parallel, to the direction of the longitudinal axis of the fiber-optic cable.

Surgical probes that control dispersive radial and axial emission find use in photodynamic therapy, especially at low powers on the order of milliwatts. Probes similar to but more durable than the ones used in photodynamic therapy (PDT) find use in hyperthermia, in which powers of an order of magnitude of watts are usual, and a power of 30 watts is not unusual. It is also possible to enhance the effect of photodynamic therapy by concurrent use of hyperthermia. A probe suitable for hyperthermic treatment, however, must be able to withstand the temperatures that are produced for the therapy.

In order to produce a useful output for these and other purposes, it is necessary to alter the direction of the laser light from an axial to a radial direction and to ensure that the intensity of the emitted beam is smooth and uniform, with an absence of "hot spots".

U.S. Pat. No. 4,592,353 to Daikuzono discloses a laser probe that can be used in direct, interstitial contact with tissue. The laser energy is coupled into the probe, which has no cladding. A coolant is applied to the junction, or gap, between the probe and the fiber-optic cable. Such probes have been used for interstitial coagulation and necrosis of tumors. Such procedures draw on principles of hyperthermia for tumor destruction. This probe, however, emits light from the end of the probe, using a lens to disperse the light in a cone with a whole angle of no more than 45E.

U.S. Pat. No. 5,380,318, also to Daikuzono, discloses a contact probe that disperses the emitted light in directions other than forward along the longitudinal axis of the fiber-optic. In one embodiment the probe is conical, and the external surface of the probe is roughened or is coated with irregularly-shaped transparent particles that will scatter the light. In another embodiment, the probe is a hollow tube or cap, and the inner surface of the cap is roughened or frosted. While these probes are more effective than the probes in Daikuzono '353 in diverting the laser energy from an axial direction to a radial one, they still emit a substantial proportion of the laser energy axially forward from the tip of the probe. These devices also show a significant peak in radiation intensity level with the tip of the probe.

U.S. Pat. No. 5,520,681 to Fuller et al. discloses a probe that disperses light by means of porosity or other inclusions within the probe. While these probes disperse the laser energy, they also generate heat, which may be harnessed for therapeutic use. Absorbent inclusions may be used to increase heating.

U.S. Pat. No. 5,054,867 to Wagnieres et al. discloses an apparatus for irradiating the bronchi of a patient for use in photodynamic therapy. A fiber-optic is surrounded by a first tube of polytetrafluoroethylene (PTFE); a brass cylinder holds the fiber-optic and tube in fixed axial position. Silicone, interspersed with titanium dioxide, fills the tube, but for a small air gap next to the brass cylinder. At the distal end of the first tube is set an aluminum cylinder, the proximal face of which acts as a mirror to light that is incident upon it. The aluminum cylinder is held in place by means of a second tube of PTFE which surrounds the first tube, leaving a small annular air gap between itself and the first tube, and extending beyond the end of the first tube. A PTFE plug is inserted at the distal end of the second tube, thus helping to hold the aluminum cylinder in place. The titanium dioxide is interspersed more heavily at the ends of the silicone-filled tube, near to the distal end of the fiber-optic and to the mirror face of the aluminum cylinder, causing the central region of the inner tube to emit less of the laser radiation than its distal and proximal regions. A troughshaped reflective coating may be provided on the inside of the outer tube, to produce irradiation over only part of the circumference of the probe. This probe, having a metal reflector, will be limited in the powers that can be applied, for at high powers, the aluminum mirror face will absorb laser energy and may lead to destructive overheating.

U.S. Pat. No. 5,908,415 to Sinofsky discloses a transparent, plastic tube which surrounds and extends beyond the distal end of a fiber-optic cable. A silicone matrix, with light-scattering particles uniformly distributed therein, fills the tube. At the distal end of the tube is a reflective surface, and a plug caps the tube off. The light traveling from the fiberoptic cable to the distal end of the tube is complemented by the light that is reflected back from the reflective surface, to produce a comparatively uniform light intensity along the length of the tube. The distance between the distal end of the fiber optic and the reflective surface, and the concentration of the scattering particles, are selected to create an intensity distribution pattern that does not vary more than plus or minus 20% along the length of the tube. No air bubbles should be within the matrix. While on the one hand this fiber-optic device produces a relatively uniform radial emission and while it is relatively easy to manufacture inasmuch as it has a uniform concentration of scattering particles, on the other hand the probe depends overmuch on the back reflection from the distal end of the device in order to achieve uniformity. The load that is put on the metal reflector can lead to overheating.

U.S. Pat. No. 5,431,647 to Purcell et al. describes a fiber-optic cable the core of which is stripped of its cladding over a distal length. Over that stripped length is snugly fitted a transparent sleeve in which light-scattering particles have been embedded. The sleeve acts as an extension of the core, so that light enters the sleeve and is scattered out sideways. Abutting the distal end of the fiber-optic is a metallic mirror to reflect back the light that has not been scattered and emitted through the sleeve. The mirror is held in place by a transparent cylindrical cap which also surrounds the sleeve and which affixes to an outer buffer of the fiber-optic cable. An air gap is maintained between the cap and the sleeve, and acts like a cladding to the fiber and sleeve. Intensity distributions varying no more than plus or minus 30% are reported to be easily obtained. In this probe, however, little is done to randomize the laser energy before it reaches the distal metallic mirror, and for this reason, if high powers are used, the mirror will overheat.

U.S. Pat. No. 5,269,777 to Doiron et al. describes a fiber-optic from which the jacket has been stripped at the distal end. Abutting and extending fore of the fiber-optic is a first silicone portion. Surrounding the first silicone portion is a silicone sleeve, in which are embedded light scattering particles. The concentration of the particles may be varied to achieve uniform or otherwise specified output patterns. Within the first silicone portion can be distributed light scattering particles, whether in discrete blocks or in continuously graded or melded concentrations. A sheath surrounds the silicone sleeve and a portion of the jacket that has not been stripped from the fiber-optic cable to provide the necessary rigidity to the tip assembly. It is asserted that the output pattern is substantially independent of the divergence of the laser beam that is coupled into the fiber-optic. This probe has little in its design to prevent the forward emission of the laser energy. In practice, either it will be limited to low powers or to applications where forward emission is immaterial or desired, or else the forward emission will be reduced by a concentration of dispersant that causes a non-uniform radial emission pattern.

U.S. Pat. No. 4,660,925 to McCaughan describes a fiber-optic cable that has been stripped of its buffer and cladding at the fore end. The distal end of the fiber-optic is carefully cleaved and polished. Layers of a scattering medium are applied to the exposed portion of the fiber-optic. Each layer is inspected and polished manually to ensure a spherically uniform emission of light, with concentrations of scatterers increasing logarithmically to the fore end, thus ensuring a uniform cylindrical distribution. A tube is tightly fitted over the painted portion of the fiber-optic. No air or contaminants must enter between the tube and painted portion. Little is done in this probe to randomize the laser energy traversing the fiber-optic, and the titration of the scattering medium according to a logarithmic pattern is not easily achieved. As a result, this probe will not find application at high powers.

U.S. Pat. No. 5,947,959 to Sinofsky discloses a device in which a transparent tube is affixed to the distal end of a fiber-optic cable. The tube surrounds and extends beyond the optical fiber. The tube comprises a single chamber which is filled with a diffusive medium which incorporates light-scattering particles of a uniform concentration and which is characterized by a single dielectric constant. A metal plug, typically gold, is set at the distal end of the tube, and serves primarily to allow image-guided location of the distal end of the tube. Light that reaches the metal plug can cause it to heat, and such heat may damage the tube or surrounding tissue. A dielectric reflector consisting of a stack of layers of different, alternating dielectric constants formed on a glass substrate and is placed aft of the metal plug. The dielectric constant of the first layer is preferably greater than the dielectric constant of the diffusive medium. The interfaces between the layers reflect a high proportion of the light backward into the tube, while generating minimal heat at the interfaces. The interfaces are spaced to produce constructive interference of the backward reflected light, assuming that the light is traveling axially. Where the dielectric reflector is used with a metal reflector, the metal ensures that forward emission out of the distal end of the tube is nil to negligible, though some of the light will be absorbed by the reflector and be converted to heat. Where the dielectric reflector is used without a metal reflector, it is assumed that the amount of light that is emitted forward is insignificant and will not injure tissue or damage other instruments. However, the laser energy reaching the dielectric reflector will have been at least partly scattered and therefore there will be a wide range of incidence angles at the interfaces. Light incident at wide angles will not benefit from constructive interference, so the dielectric reflector will undesirably permit the wider-angled energy to propagate through.

Each of the above devices found in the prior art seeks to divert some or all of a laser beam from an axial direction and emission to a radial direction and emission. However, none is practical in dealing with powers that could lead to forward emission that could undesirably injure tissue fore of the device or with powers that could undesirably overheat a reflector at the distal end and thus destroy the device.

What is needed is a device which effectively randomizes the path of the laser energy as it is propagated through the radially emissive portion of the device and achieves substantially uniform radial emission (or other controlled emission patterns), but which even at high powers generates immaterial heat at the device and can control the level of forward emission to a therapeutically exiguous amount.

SUMMARY OF THE INVENTION

The invention comprises a probe that is affixed to the fore end of a fiber-optic cable. The probe comprises a tube, or protective optical cap, that attaches to the distal end of the fiber-optic. The fore portion of the fiber-optic is stripped of buffer.

In one aspect of the invention, the tube is divided into sections. Separating the sections are optical spacers or rods, which function like bulkheads. Each section is filled with a dispersing medium, preferably a transparent matrix into which a dispersing material is placed. Each dispersing medium has distinct dispersive powers.

In another aspect of the invention, the tube is divided into sections, each filled with dispersing media having distinct dispersive powers, and a reflector is provided at the distal end of the tube to reflect light back into the foremost section.

In a third aspect of the invention, the tube contains a dispersing medium and is provided at its distal end with a reflector comprising layers of material each of which has multiple indexes of refraction.

Another aspect of the invention is a method of forming such a probe, while preventing or eliminating, air bubbles in the dispersing medium.

To achieve uniform radial emission with respect to the first two aspects of the invention, the density of the dispersing material, or dispersant, ranges from least dense at the section abutting the distal end of the fiber-optic, to most dense at the section at the distal end of the tube. Other emission patterns may be achieved by, among other things, varying the concentrations of dispersant, or the composition of the dispersants and hence their respective reflective, refractive and/or diffractive capacities, or by adjusting the matrix and hence the difference between its index of refraction and that of the embedded dispersant. The field of emission may be controlled by masking a surface of the probe with a reflective coating.

The bulkheads separating one section from the next are preferably formed of a transparent medium that has an index of refraction greater than the indexes of refraction of the matrixes found in any of the sections, and thus assures an index mismatch and accordingly a partial reflection. The greater the mismatch, the greater will be the Fresnel reflection. The bulkheads may have a common index of refraction, or may have different compositions and therefore different indexes, according to the desired result. Furthermore, if a surface of a bulkhead is given a partially reflective coating, then the Fresnel reflection may be further controlled and enhanced.

As the laser energy comes to each bulkhead, some of the energy is reflected back into the section through which it has just passed for further dispersion, and some portion is coupled into and refracted by the bulkhead, and transmitted into the next section. Inasmuch as the path of the laser energy will have been randomized, more will be subject to Fresnel reflection at the interface with the bulkhead than if it had not been randomized. The portion which is back-reflected runs the dispersion gauntlet again and will be substantially emitted from the section. The emission from the return path complements the emission from the forward path, helping to provide a more uniform output.

The distal end of the probe may be sealed off with a plug to protect the contents of the tube from dilution or contamination. To prevent or mitigate any unwanted forward transmission, a reflector is included aft of the plug. Optimally, a reflector is selected which interdicts the forward propagation of laser energy incident upon the reflector at wide angles.

Especially in hyperthermic procedures, the probe may be surrounded by a transparent sheath, and a fluid coolant may be circulated between the probe and the sheath, thus cooling both the tissue and the probe.

The Fresnel reflection at the bulkheads reduces the amount of laser energy that reaches the distal reflector, and thus mitigates heating at the distal end and/or forward emission. The Fresnel reflection further smoothes the gradient of radial emission that would otherwise result at the junction of sections of differing dispersive capacities.

In certain applications, however, especially ones requiring low powers, use of a distal reflector that does not overheat and that effectively reflects light having wide angles of incidence may obviate the need for bulkheads and even varying the concentration of the dispersant. As the active length L of the probe increases, a single concentration of dispersant may not be sufficient to yield uniform radial emission. In such a case, it is possible to vary the concentration of the dispersant. It is also possible to have discrete sections of matrix (with no intervening spacers) where the matrixes have differing indexes of refraction, and thus cause backward reflections and increase the optical path. Conversely, in such low-power applications or applications where emission of light forward from the probe is acceptable, the use of bulkheads may obviate the need for a distal reflector.

All the materials used in the probe should in general exhibit little absorption of light and therefore generate minimal to no unwanted heat. The principal exception to this constraint occurs in low-power applications. In such applications, the reflector may be a metallic reflector.

According to one aspect of the invention, a light-emitting probe comprises a flexible, light-transmissive housing having a proximal end, adapted to be mounted to and to receive light from a fiber-optic, and a closed distal end; at least one optical spacer dividing the length of the interior of the housing into at least two sections such that the most proximal section abuts the fiber-optic; and a light-transmissive and light-dispersing medium filling each section.

The housing and the light-dispersing medium are preferably light-transmissive in the sense that they permit light to pass through them without significant absorption, and thus without the heating that would result from the absorbed energy. The light-transmissive housing may be, but need not be, transparent in the sense that a clear image could be seen through it. Because the light passing through the housing has already been dispersed by the light-dispersing medium, there is usually no need to avoid further dispersion as the light passes through the housing. The light-transmissive housing and the light-transmissive and light-dispersing medium need to be transmissive only to light of the frequency that is intended to be used with the particular probe. Thus, where the probe is intended to be used with infra-red light, the housing and the light-dispersing medium are not necessarily light-transmissive in visible light.

The probe may comprise a reflector at the distal end of the most distal said section. The reflector may comprise a metal layer. The reflector may comprise a mirror of thin reflecting film layers. Individual ones of the thin layers may be reflecting, and the thin layers may then be layers of silver film. Instead, the layers may be reflecting only in combination, for example, because of changes in refractive index at the boundaries between adjacent layers.

The probe may further comprise a sheath surrounding said probe and arranged in use to be supplied with a coolant liquid. The probe may then further comprise a catheter surrounding the optical fiber-optic and defining channels to supply and remove said liquid coolant.

According to another aspect of the invention, a light-emitting probe comprises: a flexible, light-transmissive housing, having a proximal end adapted to be connected to a source of laser light and a distal end. There is a light-transmissive and light-dispersing medium within the housing, divided along the length of the housing into at least two sections having distinct light-dispersing properties. A reflecting means at the distal end of the housing is arranged to reflect light back into the light-transmissive and light-dispersing medium.

A further aspect of the invention provides a light-emitting probe comprising a flexible, transparent housing, having a proximal end adapted to be connected to a source of laser light and a distal end. A light-transmissive and light-dispersing medium is within the housing. A reflector at the distal end of the housing is arranged to reflect the light back into the light-dispersing medium. The reflector comprises layers designed to reflect the light back into the housing and exhibits multiple indexes of refraction at each layer.

For any aspect of the invention, coolant may be delivered via a catheter to abstract adventitious heat. Coolant serves a further purpose: a premature build-up of heat within the tissue adjacent to the probe is prevented. Were the tissue to overheat to the point of charring, the char would obstruct the further desired penetration of the laser energy and compound the overheating and lead to the possible destruction of the probe.

BRIEF DESCRIPTION OF THE DRAWINGS

For the purpose of illustrating the invention, there are shown in the drawings forms of the invention which are presently preferred; it being understood, however, that this invention is not limited to the precise arrangements and instrumentalities shown.

DETAILED DESCRIPTION OF THE DRAWINGS

Figure 1:
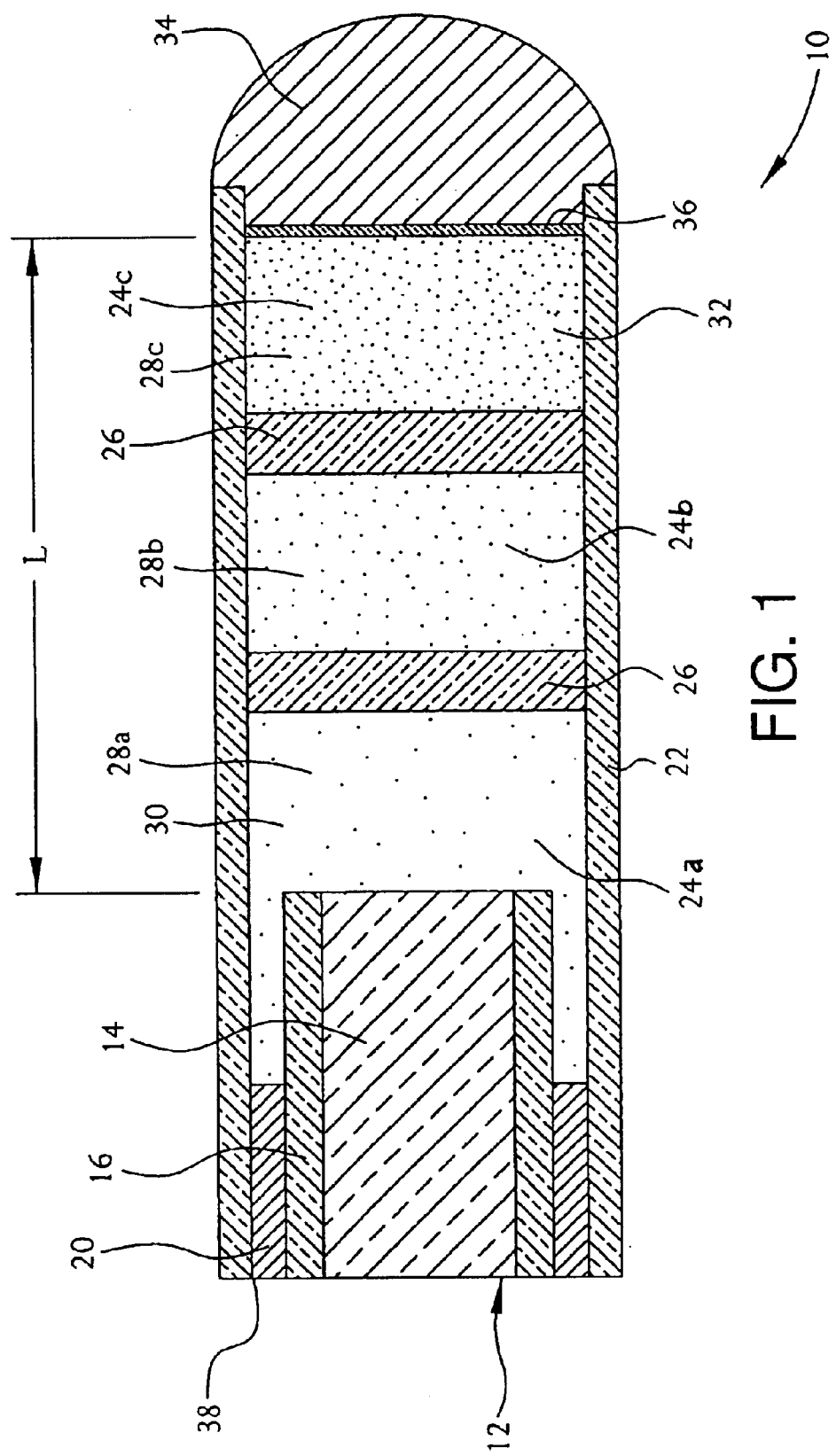
FIG. 1 shows an axial sectional view of one form of probe embodying the invention. In the interests of clarity, the widthwise dimensions have been greatly enlarged in comparison with the lengthwise dimensions.

Referring to FIG. 1, one form of probe according to the invention, indicated generally by the reference numeral 10, is attached to the distal (foremost, or tip) end of an optical fiber 12 comprising a core 14 surrounded by a cladding 16. Surrounding the optical fiber is a fiber buffer 20 made of a plastic known as TEFZEL® (a registered trademark of E. I. DuPont de Nemours, Wilmington, Del.). The front faces of the core 14 and the cladding 16 are cleaved flat. The buffer may be cleaved flush with the front faces of the core and clad, or it may be cleaved and removed aft of those front faces. If it is removed aft (as shown in FIG. 1), then it may be filled with matrix and dispersant from the first section 28a, as described below. A tube 22 surrounds the front end of the fiber buffer 20 and extends forwards of the distal end of the optical fiber 12. The tube 22 overlaps the fiber buffer 20 by a distance sufficient to give strength to the bond between the tube and the fiber-optic cable, and is bonded to the fiber buffer by adhesive.

The space within the tube 22 forward of the end of the optical fiber 12 is separated into three sections, 24a, 24b, and 24c by two optical spacers in the form of bulkheads 26a and 26b. Each section 24a, 24b, and 24c is filled with a light-transmissive and light-dispersing medium 28a, 28b, and 28c, respectively. The dispersing medium consists essentially of a transparent matrix 30, symbolized in the drawings by the clear area in each section 24a, 24b, and 24c, which in turn has interspersed within itself a dispersive material or dispersant 32 symbolized by the dots strewn within each section. An end plug 34 closes the tube 22 forward of the front (most distal) section 24c. Reflecting means 36 lies between the end plug 34 and the front section 24c. The distance L from the cleaved end face of the core 14 to the proximal face of the reflecting means 36 is the active length of the probe.

The fiber-optic cable, comprising the core 14, the cladding 16, and the fiber buffer 20, and including the extra width of the tube 22, is slim enough that it is still able to slip down a working channel of a catheter, cannula or endoscope, typically having outer diameters in the range of 7 French. In the preferred case, the outer diameter of the core 12 is 600 microns, or 0.6 mm, and the outer diameter of the fiber buffer 20 is 750 microns, or 0.75 mm. Smaller cores (e.g. 400 microns) are also preferred. A fiber-optic cable composed of silica is usually suitable for transmitting the laser energy. The laser energy typically used will be over a range of wavelengths that penetrate tissue and coagulate it. The wavelength of 1,064 nm of the Nd:YAG laser is such a wavelength, as are 940 nm and 980 nm generated by diode lasers, and silica is transparent at those wavelengths. However, the invention is not restricted to the use of near-infrared laser light, but can also be applied in the visible region of light spectrum, so long as the frequency of light chosen is compatible with the materials of the probe and answers the therapeutic need.

The tube 22 is composed of polytetrafluoroethylene (PTFE), commonly known as TEFLON, which a registered trademark of E. I. DuPont de Nemours (Wilmington, Del.). PTFE is a suitable material for the tube inasmuch as it is flexible, biocompatible and optically transparent and exhibits little absorption of light and attendant heating. The PTFE tube 22 constitutes a light-transmissive housing for the probe 10. The tube 22 extends beyond the distal end face of the core 14 by a length L, called the active length of the probe; in the case depicted the working length is 30 mm. The outer diameter of the tube 22 is 1.1 mm. The tube 22 extends aft of the cleaved distal end face of the core 14 for a length of 15.75 mm (0.62 inches), in order to give strength to the bond between the tube and the fiber-optic cable 12. The tube 22 is attached to the fiber-optic cable by means of an adhesive 38. One such adhesive is Dymax 1128-M, an ultraviolet-curable medical-grade adhesive available from Dymax Corp. (Torrington, Conn.).

Silicone epoxy has been found to be suitable for the transparent matrix 30. One suitable material is Mastersil 151 Clear, a silicone epoxy having an index of refraction of 1.43, which can be obtained commercially from Master Bond, Inc. (Hackensack, N.J.).

It is possible, though not usually necessary, to vary the choice of matrix from section to section, just as it is also possible, though not usually necessary, to vary the choice of dispersant from section to section. The index of refraction of the matrix and the dispersant may be the same, or different. The matrix and the dispersant, like all other materials of the probe, should usually have a nearly null imaginary index of refraction, and thus have little to no absorption leading to attendant heating. The principal exception is in low-power applications, as for example PDT, where a significant proportion of the laser energy can be absorbed without causing excessive heating. In such applications, a metallic mirror reflector may be used as reflecting means 36, discussed below.

It is important, however, that the dispersant 32 should lie in the path of the laser energy before that energy reaches the distal end 34, 36 of the probe. The dispersant 32 assures that the path of the laser energy is randomized. If it is desired to achieve a uniform radial emission, the density of the dispersant 32 is least at the section 24a abutting the optical fiber 12 and greatest at the distal end 36 of the active length L of the probe. The capacity to disperse light, and hence the transmissivity, of each section 24a, 24b, 24c, will thus differ from that of the other sections.

Particles of titanium dioxide, aluminum oxide or silicon dioxide have been found to be suitable materials for the dispersant 32. The dispersant depicted in FIG. 1 is titanium dioxide, available in the form of titanium-dioxide-filled silicone epoxy such as Mastersil 151 White, from Master Bond. The titanium dioxide particles are optimally in rutile crystalline form and have an index of refraction of 2.73. Silicone has a refractive index of 1.43. In the preferred embodiment, laser energy at 1,064 nm from an Nd:YAG laser is used to treat tumorous growths, but diode wavelengths of 940 nm and 980 nm can also be used. Preferably, the particles should be less than 1 micron in diameter. The ratio of Mastersil 151 Clear to Mastersil 151 White, by weight, in sections 24a, 24b and 24c is 3,000:1, 1,900:1 and 1,200:1, respectively, for a 30 mm active length L. In Mastersil 151 White, there are 30 grams of titanium dioxide for every 300 grams of silicone.

Separating the sections are the bulkheads 26a and 26b. The bulkheads are disc-like wafers or rods, measuring 750 microns in diameter (and 490 microns in a smaller tube variation) and 1 to 1.5 mm in length. The discs 26a, 26b are highly polished on surfaces normal to the longitudinal axis. They are fitted snugly between the dispersing media 28a, 28b, 28c filling the sections 24a, 24b, 24c.

Air pockets should be strictly avoided, as they create destructive heat. Two steps have been found especially helpful as a method of avoiding air pockets. In the first preferred step, the matrix 30 and dispersant 30 are mixed to be completely homogeneous, without streaks or swirls. During mixing, the selection of matrix and dispersant is subjected to a gauge vacuum of 25 mm of mercury. The vacuum induces air that may be latent within the selection to froth at the surface of the mixture. The vacuum is then broken quickly, and as a result, the air bubbles that were induced to the surface burst into the atmosphere. This process is repeated until there are no streaks or swirls in the admixture and until there is no more frothing of air.

In the second preferred step, the tube 22 is mounted onto the optical fiber 12, and the dispersing media 28a, 28b, 28c and the bulkheads 26a, 26b are assembled into the tube in order from the proximal (optical fiber) end towards the distal end 34, 36. The silicone epoxy matrix of the dispersing media 28a, 28b, 28c is in an unset, thickly liquid state in which it fills the space within the tube 22. The selection 28a of matrix and dispersant that is to be inserted first into the tube 22 is inserted under positive pressure. This first batch is carefully inspected for trails of latent air within the zone of the tube 22 to which ultraviolet-curable adhesive 38 is applied.

Under magnification and with a sharp needle (e.g. Dritz beading needle size no. 10/13 or Schmetz Microtex sharp needle 130/705 H-M 80/12), a puncture is made at the most proximal point of the most prominent air trail; in some cases, two punctures may be needed. The puncture is made in the part of the tube 22 where the dispersing medium 28a surrounds the stripped part of the optical fiber 12, behind the end face of the core 14. Thus, if the puncture creates an optically significant blemish in the finished probe, it is in a region where no significant dispersion of light is occurring, and does not affect the performance of the probe. As the end plug 34 is finally inserted into the tube 22, it acts as a piston and purges latent air out of the punctures. Matrix and dispersant will follow the air that is expressed through a puncture, and will seal such puncture as it hardens. Care should be taken not to puncture the fiber buffer 20 surrounding optical fiber 12.

Cubic zirconium has been found to be a preferred material for the bulkheads 26a, 26b. Its index of refraction is 2.12, which is suitably higher than the 1.43 of the silicone epoxy medium. It is optically isotropic, so that there are no constraints on orientation of axes due to polarization, and it sustains little loss to absorption and other causes. Cubic zirconium is available from Imetra, Inc. (Elmsford, N.Y.). Aluminum oxide (sapphire) can also be used as a suitable bulkhead.

It is desirable that the index of refraction of each bulkhead 26a, 26b be greater than the greatest index of refraction found in any section 24a, 24b, 24c. Subject to that, the bulkheads may share a common material and therefore a common index of refraction, or they may have differing composition, and thus differing indexes of refraction. The bulkheads exhibit low absorption and high internal transmissivity. The index of refraction of the tube 22 is to be less than any of the indexes of refraction of the sections. PTFE is the preferred material for the tube, and its index of refraction is 1.31. A lesser index of refraction promotes further internal reflection, which is necessary to extend the radial emission over a greater active length L of the probe.

Laser energy propagates through probe 10 as follows. The light is coupled from the distal face of the optical fiber core 14. Depending on a number of factors, including the length of the fiber-optic cable, it will typically have a fill-angle divergence of up to approximately 46 degrees where the numerical aperture of the fiber is 0.39 and approximately 57 degrees where the numerical aperture of the fiber is 0.48. The bulk of the laser beam, however, will diverge from the longitudinal axis of the core 14 only by several degrees, and thus the angular distribution of the beam will assume a Gaussian pattern. The index of refraction of the core 14 is that of silica, or 1.45; the index of refraction of the medium 28a in the section 24a is two-fold: an index of 1.43 for the silicone 30, and an index of 2.73 for the titanium dioxide 32. The laser beam, as it is coupled into and through the section 24a, is immediately dispersed and randomized.

A portion of the randomized light hits the wall of the tube 22, and if the angle of incidence of the light (measured from the normal to the incident surface) is less than the critical angle between the medium 28a and the tube 22, the light couples into and through the tube. The amount of light energy remaining within the tube 22 is greatest at the proximal region of section 24a, and tapers off to the least amount at the distal region of the section. The amount of light that is emitted out of tube 22 also tapers off from the proximal region of the section to the distal region of the section, in dependence on the amount of light in the tube and the scattering of that light.

The laser energy that propagates through section 24a and reaches the proximal face of bulkhead 26a is subject to Fresnel's law. Because the light has been scattered, the percent reflection due to Fresnel's Law increases, because the angle of incidence is increased. In addition, the greater the difference between the indexes of refraction of section 24a and bulkhead 26a, the greater is the proportion of the light that is reflected. In the probe shown in FIG. 1, the difference in refractive index is approximately 0.69 (i.e., 2.12–1.43). The measured Fresnel reflection for normal incidence is on the order of 4% at each face or boundary interface of the bulkhead. The light reflected back into section 24a will be emitted similarly to the light propagating forward as described above, and the amount of emitted light will taper in the reverse direction, with the amount being greatest near the bulkhead 26a and least near the end face of the optical fiber. The reversely tapering emission will complement and superimpose on the forward tapering pattern of the unreflected light. For practical purposes, the reflected light becomes trapped in the section 24a, so that it does not couple into other sections, until it is emitted radially from that section.

As the light couples from the first bulkhead 26a into the next section 24b, the amount emitted typically rises at the interface, and then tapers off towards the interface with the second bulkhead 26b. The initial rise would be all the more pronounced, were it not for the back-filling performed by the Fresnel reflection from bulkhead 26a back into the first section 24a.

Given that the proximal and distal faces of the bulkhead 26a are parallel, the light will couple out and continue in the same direction in which it was coupled into the bulkhead. However, if the faces of the bulkhead are not parallel to each other and/or are not normal to the longitudinal axis of the fiber-optic, the light propagating from the distal face of bulkhead 26a will take a different path.

As the light traverses through succeeding sections and bulkheads, similar effects are achieved to those described above for the first section 24a and the first bulkhead 26a. Thus, in each section, there is an emission of forward-propagating light, which is greatest at the proximal end of the section, and an emission of reflected light, which is greatest at the distal end of the section and which is superimposed on the emission from the forward-propagating light. The absolute intensity of light in the tube decreases from each section to the next. The density of the dispersant 32 can be increased in each successive section, so as to increase the proportion of light scattered out of the tube. It is possible by this means to keep the absolute amount of light emitted from different parts of the tube uniform, if that is desired. Other light distributions can be achieved by a suitable selection of the amount of dispersant 32 in each tube section 24.

In any embodiment of the bulkheads, one may apply a partially reflective coating 262 (see FIG. 3) to either the proximal or the distal face of any of the bulkheads, or to both faces, in order to enhance the back reflection of the light. Such coatings are available commercially from numerous suppliers. One such supplier is Spectrum Thin Films (Bohemia, N.Y.).

When the light propagates through the most distal section 24c, a portion of it will reach the reflecting means 36 formed on the plug 34. For any light that has not been coupled out of the tube 22 by the time it reaches the distalmost part of the foremost section, the reflecting means 36 stands ready to return the light to the prior section. The substantial majority of the light incident on the reflecting means 36 is reflected back into the last section 24c. The reflector 36 thus prevents the waste of energy that can be rendered therapeutic. Together with the end cap 34, it also protects surrounding tissue from needless injury and adjacent instruments from needless damage that might be caused by the laser light beam escaping through the tip of the probe 10.

The reflected light follows the laws of reflextion and the angle of reflection equals the angle of incidence. The returning light undergoes the same scattering by the sections and partial reflection by the bulkheads as the forward path underwent. The light emitted after reflection by the reflecting means 36 further complements that emitted on the forward path. The uniformity in the emission of light from the tube 22 along the length of each section is dependent to a large extent on the balance between the amounts of light entering that section from the proximal and distal ends. The partial reflection at the bulkheads 26a, 26b, thus reduces the amount of light that must reach and be reflected by the reflector 36 to maintain any desired degree of uniformity in the emission of light from the active length L of the tube. The reduction in the amount of light reaching the reflector 36 in turn reduces the absolute amount of light absorbed by the reflector, and thus reduces heating of the end plug 34 by the absorbed light.

The plug 34 is a mushroom-shaped cap. It can be made of optical-grade, biocompatible materials, as for example. HP2R Lexan, obtainable from GE Plastics (Pittsfield, Mass.). Its dimensions are conformed to fit the tube 22 in which it is installed. It is affixed to the distal end of tube 22 by an adhesive.

The plug 34 serves two purposes. First, it protects the interior of tube 22 and the enclosed sections 24 from invasion by influents. Second, it provides a base on which the reflecting means 36 can be applied.

The reflecting means 36 is preferably a reflective coating which, as generally understood, will reflect backward a substantial majority of light impinging on it and will not absorb that light or otherwise generate unwanted heat. As shown in FIG. 1, the reflective coating 36 comprises a mirror of thin layers of reflective film. Individual layers may be reflective, or the layers may be reflective in the aggregate, for example, dielectric layers with alternating dielectric constants. It is not critical that the light reflecting backward from the different layers should benefit from constructive interference. As noted above with reference to the Sinofsky '959 reference, a constructive interference reflector consisting of a stack of quarter-wave-thickness layers may provide very good reflection of light rays traveling parallel to the axis, but may not efficiently reflect scattered light. In practice, it is feasible to use a reflector of layers having thicknesses approximately equal to a quarter of the average of the wavelengths that may be propagated through the probe. Such a range may be from 940 nm to 1,064 nm, as this range of wavelengths exhibits generally good penetration of tissue. Reflection coatings are available at numerous facilities. One such facility is Spectrum Thin Films.

In a preferred embodiment, the reflector 36 consists of a plurality of layers of birefringent or other material that exhibits multiple indexes of refraction within the layers. The reflector can thus be better able to control and redirect light of widely varying angles of incidence. Such reflectors are described in U.S. Pat. No. 6,101,032 to Wortman et al. Reflectors exhibiting such properties are available from 3M Corporation (Minneapolis, Minn.) and can be applied to a substrate such as glass or plastic (e.g. polyester) and in-set between the foremost section 24c and the end plug 34.

If some portion of the light should emerge from the reflecting means 36 and out of the plug 34, it must be of an intensity and direction that does not injure the tissue it impinges on or damage any attendant instruments. In one empirical test, the forward transmission from three dispersive probes was measured. The probes had no distal reflecting means and were substantially the same, except in the number of spacers. The first probe had two spacers (distal and proximal), positioned to divide the probe into three nearly equal sections, viz. proximal, medial and distal. The forward transmission was 26.5%, relative to the energy introduced into the proximal end of the probe. The second probe (with one spacer) was like the first, except that where the first probe had a proximal spacer, the second probe had no spacer dividing the medial and proximal sections. The forward transmission of this probe was 38.3%, relative to the energy introduced into the proximal end of the probe. Finally, the third probe had no spacers dividing the proximal, medial and distal sections. Its forward transmission was 46.3%. The bulkheads manifestly reduce the amount of forward transmission of the dispersive probe.

In applications where low powers are used, as in PDT applications, a metallic mirror reflector may be used as the reflecting means 36. Gold is a preferred metal, because of its low chemical reactivity. It can be applied in various ways to the proximal surface of the plug 34 (e.g. by vapor or ion beam deposition), or a thin disc of gold can be set between the plug 34 and the foremost section 24c. Silver can also be used but it should be given an overcoat, as for example of silica, to prevent its oxidation. In fact, if an overcoat of thin reflecting film layers is applied, the silver not only is protected from oxidation, but also is able to operate at higher powers than gold alone. If desired, a cooling sheath from a catheter, as described below with reference to FIG. 3, can to be used to abstract heat generated by the metallic surfaces.

Each bulkhead 26 thus serves several functions. First, each bulkhead acts as a checkpoint of the propagating laser beam. Some portion of the beam is reflected back at each bulkhead 26, thus reducing the amount of light reaching the reflecting means 36. As such, the potential for forward emission is reduced. Second, each bulkhead smoothes the gradient of emission between two sections. Third, each bulkhead separates the contents 28 of adjacent sections 24a, 24b, 24c and thus prevents intermingling and preserves the different concentrations of the dispersant 32 in the different sections.

In applications requiring low powers, the use of a distal reflecting means 36 that is effective in reflecting light having wide angles of incidence may obviate the need for bulkheads 26. On the other hand, in such low-power applications or in applications where limited forward emission of light is acceptable, then the use of bulkheads 26 may obviate the need for a distal reflecting means 36.

Figure 2:
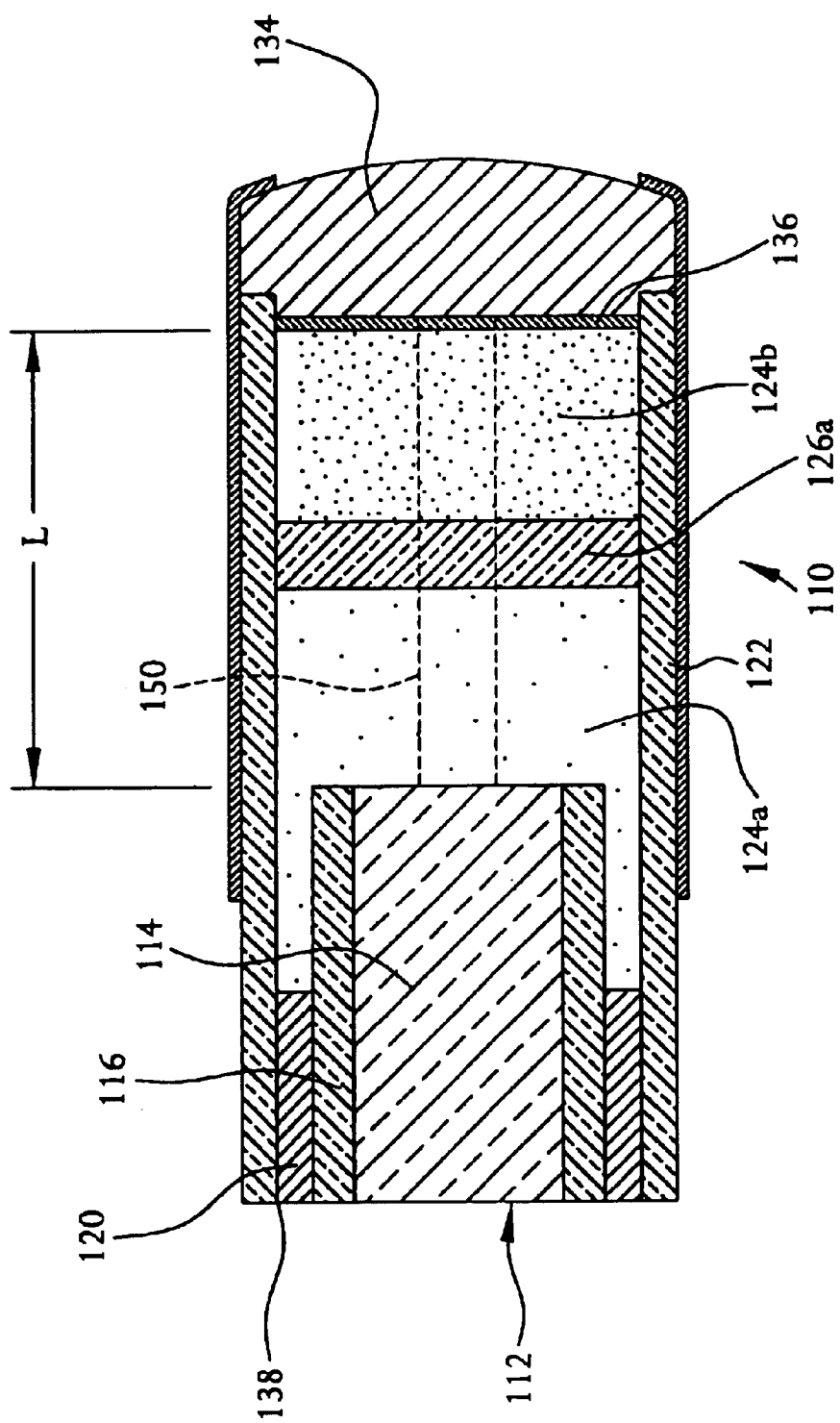
FIG. 2 shows a view similar to FIG. 1 of a second form of probe embodying the invention.

Referring to FIG. 2, the second embodiment of the invention is generally similar to the first embodiment shown in FIG. 1, and features embodied in FIG. 2 that are common with features in FIG. 1 share like numbers, increased by 100. Thus, a probe 110 in FIG. 2 is attached to an optical fiber 112 having a core 114 surrounded by cladding 116, encased within a buffer 120. A tube 122, an end cap 134, a reflector 136, and so on, may be substantially the same as those described above with reference to FIG. 1. However, the probe 110 shown in FIG. 2 has only one bulkhead 126a and only two light-dispersing sections, 124a and 124b.

As shown in FIG. 2, a portion of the external surface of the first section 124a within the working length L has been masked by reflecting means 150. The reflecting means 150 is in a stripe extending over the whole active length of the probe. The purposes of the reflecting stripe is to return the laser energy back into the section, and thus restrict the emission of laser energy to a portion of the tissue that is adjacent to the cylindrical wall of the tube. Such probes may be useful in lumens where only a limited sector of the lumen requires irradiation. The buffer of the fiber-optic can be given a stripe that is coaxial with the reflecting stripe and thus enable the surgeon to orient the probe correctly. The stripe 150 consists of a reflective coating applied to the outside of the tube 122. Such coatings are available from numerous suppliers. One such supplier is Spectrum Thin Films (Bohemia, N.Y.). If necessary, a plastic sleeve (not shown) may be applied, as for example by heat-shrinking, to protect the coating. Alternately, the reflective stripe may be applied to an internal surface of the probe.

Figure 3:
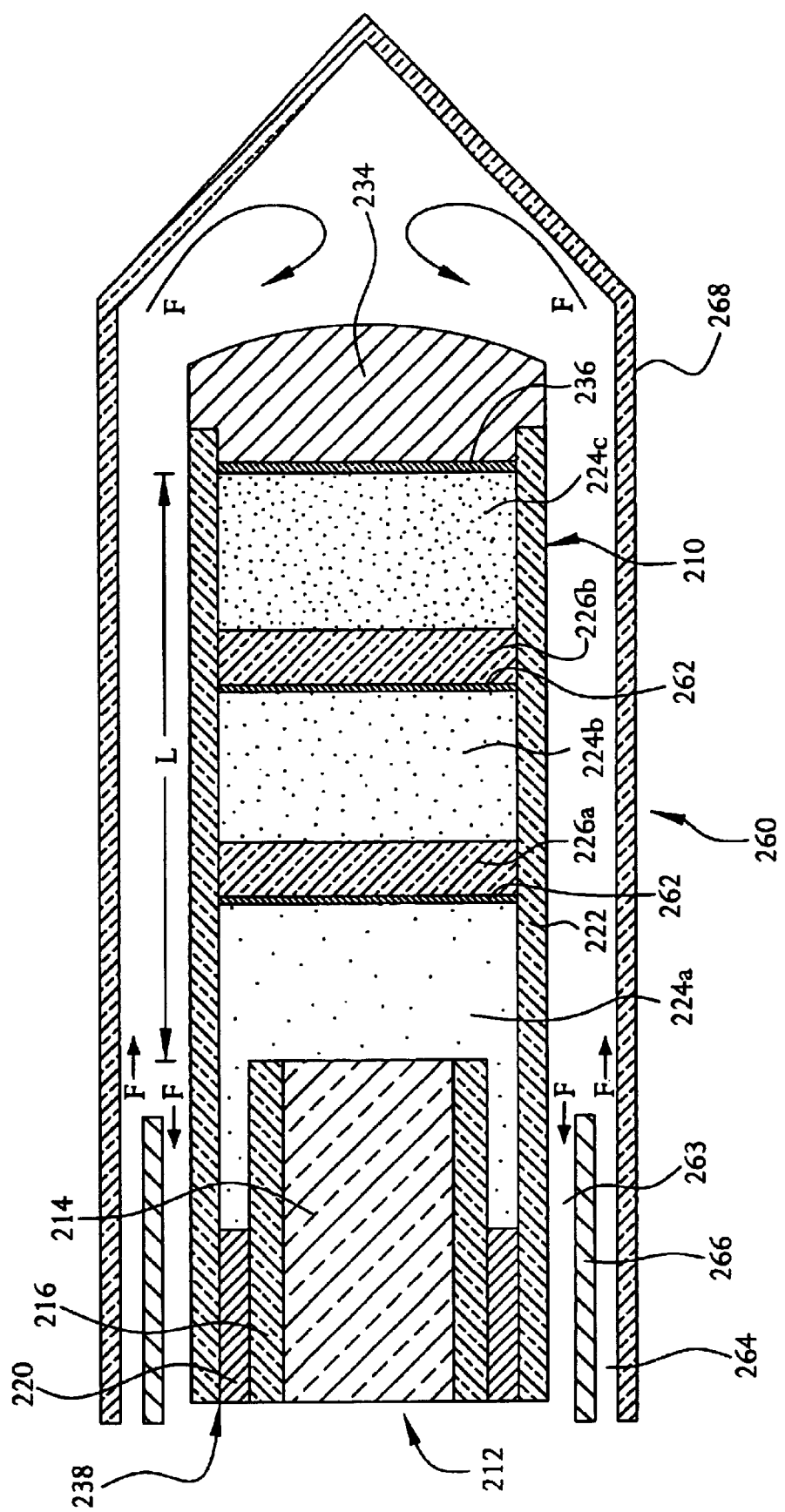
FIG. 3 shows a view similar to FIG. 1 of a third form of probe embodying the invention.

Referring now to FIG. 3, the third embodiment of the invention comprises a probe 210 in combination with a catheter indicated generally by the reference numeral 260 providing liquid cooling of the probe tip. The probe 210 shown in FIG. 3 is generally similar to the first embodiment shown in FIG. 1, and features embodied in FIG. 3 that are common with features in FIG. 1 share like numbers, increased by 200. Thus, the probe 210 is attached to an optical fiber 212 having a core 214 surrounded by cladding 216, encased within a buffer 220. A tube 222, an end cap 234, and so on, may be substantially the same as those described above with reference to FIG. 1. In this embodiment, however, the reflecting means 236 is a metallic mirror surface applied on the plug 234, and a partially reflecting means 262 has been applied to the proximal face of each of the bulkheads 226a and 226b that separate the sections 224a, 224b, and 224c. A similar reflective coating may also be applied to the distal faces of the bulkheads 226, or a coating may be applied to only the distal face of a bulkhead.

The catheter 260 has an inner working channel 263, in which the fiber-optic cable 212 and the probe 210 have been inserted, and an outer working channel 264. The channels 263 and 264 are separated by a tube 266. The distal end of the tube 266 is just short of the distal end of the optical fiber 212. The outer wall of the catheter 260 is formed by a plastic sheath 268 that is transparent to the treatment laser wavelength, which is closed at its distal end and encloses the probe 210. The sheath 268 thus defines a plenum 270, which surrounds the active length L of the probe 210 and is open to both of the working channels 263 and 264. Fluid coolant, which may be, for example, sterile water can be delivered to the plenum 270 through the outer working channel 264, allowed to swirl freely within the plenum, and withdrawn through the inner working channel 263, as shown by the arrows F in FIG. 3.

The coolant serves two purposes. First, it prevents the tissue adjacent the sheath 268 and proximate to the active length L from overheating. If the tissue should overheat, it may char or otherwise impede the penetration of the laser energy into the tissue to be coagulated. Second, the coolant prevents the active length L, including the reflecting means 236 and 262 and the plug 234, from overheating. The coolant carries off such heat as it is conducted from the surgical site via the inner working channel 263. The coolant has no direct contact with the tissue being treated.

A suitable catheter, called Irrigated Power Laser Applicator Kit, is available commercially from Somatex® Medizintechnische Instrumente (Rietzneuendorf/b. Berlin, Germany).

The present invention may be embodied in other specific forms without departing from the spirit or essential attributes thereof and, accordingly, reference should be made to the appended claims, rather than to the foregoing specification, as indicating the scope of the invention.

For example, although the probe 10 shown in FIG. 1 and the probe 210 shown in FIG. 3 have three light-emitting sections 24 and the probe 110 shown in FIG. 2 has two light-emitting sections, any of those probes may have a different number of sections, depending on the requirements of a particular application. It will be appreciated by those skilled in the art that a greater number of sections can allow a more precise control over the distribution of emitted light along the length of the probe, but that a smaller number of sections allows simpler manufacture and a more economical product.

What is claimed is:

1. A light-emitting probe comprising:
    a flexible, light-transmissive housing having a proximal end, adapted to be mounted to and to receive light from a fiber-optic, and a closed distal end;
    at least one optical spacer dividing the length of the interior of the housing into at least two sections such that the most proximal section abuts the fiber-optic; and
    a light-transmissive and light-dispersing medium filling each section;
    wherein the index of refraction of the at least one spacer is greater than the index of refraction of the light-transmissive and light-dispersing medium.

2. A probe according to claim 1, wherein the light-transmissive and light-dispersing medium comprises a light-dispersing material in a light-transmissive matrix.

3. A probe according to claim 1, wherein said light dispersing medium in different said sections has different dispersing powers.

4. A probe according to claim 1, wherein said light dispersing medium in different said sections comprises different concentrations of a light-dispersing material in a light-transmissive matrix.

5. A probe according to claim 1, further comprising a reflector at the distal end of the most distal said section.

6. A probe according to claim 5, wherein the reflector comprises a metal layer.

7. A probe according to claim 5, wherein the reflector comprises a mirror of thin layers of dielectric film.

8. A probe according to claim 5, wherein the reflector comprises layers designed to reflect the light back into the housing and exhibits multiple indexes of refraction at each layer.

9. A probe according to claim 1, wherein the housing is transparent.

10. A probe according to claim 9, wherein the housing comprises a transparent tube sealed off by a plug at the distal end.

11. A probe according to claim 10, further comprising a reflector formed on the end plug.

12. A probe according to claim 1, wherein the light-transmissive housing is a housing that is substantially non-absorptive of light passing through it.

13. A probe according to claim 12, wherein the housing is light-transmissive for infra-red light with a wavelength in the range from 940 to 1064 nm.

14. A probe according to claim 13, further comprising a catheter surrounding the fiber-optic and defining channels to supply and remove said coolant liquid.

15. A probe according to claim 12, further comprising a sheath surrounding said probe and arranged in use to be supplied with a coolant liquid.

16. A probe according to claim 1, further comprising a partially-reflecting layer on at least one end face of said at least one optical spacer.

17. A probe according to claim 1, further comprising a fiber-optic adapted to conduct light from a source and to which the proximal end of the housing is mounted.

18. A light-emitting probe comprising:
    a flexible, light-transmissive housing having a proximal end, adapted to be mounted to and to receive light from a fiber-optic, and a closed distal end;
    at least one optical spacer dividing the length of the interior of the housing into at least two sections such that the most proximal section abuts the fiber-optic;
    a light-transmissive and light-dispersing medium filling each section; and
    a reflector at the distal end of the most distal said section;
    wherein the reflector comprises a birefringent material.

19. A light-emitting probe, comprising:
    a flexible, light-transmissive housing, having a proximal end adapted to be connected to a source of laser light and a distal end;
    within said housing a light-transmissive and light-dispersing medium, divided along the length of said housing into at least two sections having distinct light-dispersing properties; and
    a reflector that comprises a birefringent material at the distal end of said housing arranged to reflect the light back into the light-dispersing medium.

20. A probe according to claim 19, wherein the light-transmissive and light-dispersing medium comprises a light-dispersing material in a light-transmissive matrix.

21. A probe according to claim 20, wherein said light-dispersing medium in different said sections comprises different concentrations of said light-dispersing material in said light-transmissive matrix.

22. A probe according to claim 19, wherein the reflector comprises a mirror of thin reflecting film layers.

23. A probe according to claim 19, wherein the reflector comprises layers designed to reflect the light back into the housing and exhibits multiple indexes of refraction at each layer.

24. A probe according to claim 19, wherein the housing is transparent.

25. A probe according to claim 24, wherein the housing comprises a transparent tube sealed off by a plug at the distal end.

26. A probe according to claim 25, wherein the reflector is formed on the end plug.

27. A probe according to claim 19, wherein the light-transmissive housing is a housing that is substantially non-absorptive of light passing through it.

28. A probe according to claim 27, wherein the housing is light-transmissive for infra-red light with a wavelength in the range from 940 to 1064 nm.

29. A probe according to claim 19, further comprising a fiber-optic adapted to conduct light from a source and to which the proximal end of the housing is mounted.

30. A probe according to claim 29, further comprising a sheath surrounding said probe and arranged in use to be supplied with a coolant liquid.

31. A probe according to claim 30, further comprising a catheter surrounding the fiber-optic and defining channels to supply and remove said coolant liquid.

32. A probe according to claim 19, further comprising at least one optical spacer separating said at least two sections.

33. A probe according to claim 32, further comprising a partially-reflecting layer on at least one end face of said at least one optical spacer.

34. A probe according to claim 32, wherein the index of refraction of the at least one spacer is greater than the index of refraction of the light-transmissive and light-dispersing medium.

35. A light-emitting probe comprising:
- a flexible, light-transmissive housing having a proximal end, adapted to be mounted to and to receive light from a fiber-optic, and a closed distal end;
- at least one optical spacer dividing the length of the interior of the housing into at least two sections such that the most proximal section abuts the fiber-optic; and
- a medium comprising a light-dispersing material in a light-transmissive matrix filling each section;

wherein the index of refraction of the at least one spacer is greater than the index of refraction of the light-transmissive matrix.

36. A probe according to claim 35, wherein the index of refraction of the light-dispersing material is greater than the index of refraction of the at least one spacer.

37. A probe according to claim 35, wherein said medium in different said sections comprises different concentrations of said light-dispersing material in said light-transmissive matrix.

38. A probe according to claim 35, further comprising a reflector at the distal end of the most distal said section.

39. A probe according to claim 35, further comprising a partially-reflecting layer on at least one end face of said at least one optical spacer.

* * * * *

UNITED STATES PATENT AND TRADEMARK OFFICE
CERTIFICATE OF CORRECTION

PATENT NO. : 6,893,432 B2
DATED : May 17, 2005
INVENTOR(S) : Intintoli et al.

It is certified that error appears in the above-identified patent and that said Letters Patent is hereby corrected as shown below:

Column 2,
Line 26, change "45E" to -- 45 degrees. --.

Column 3,
Line 13, change "fiberoptic cable" to -- fiber-optic cable --.
Line 17, change "fiber optic" to -- fiber-optic --.
Line 26, change "back reflection" to -- back-reflection --.

Column 4,
Line 28, change "constants formed" to -- constants is formed --.
Line 46, change "incidence angles" to -- incident angles --.

Column 12,
Line 5, change "reflextion" to -- reflection --.

Column 14,
Line 1, change "the purposes… is" to -- the purpose… is --.

Signed and Sealed this

Thirtieth Day of August, 2005

JON W. DUDAS
*Director of the United States Patent and Trademark Office*